(12) United States Patent
Bhushan et al.

(10) Patent No.: US 10,849,508 B2
(45) Date of Patent: Dec. 1, 2020

(54) SYSTEM AND METHOD FOR CONTINUOUS MONITORING OF BLOOD PRESSURE

(71) Applicant: Fourth Frontier Technologies Pvt. Ltd., Bangalore (IN)

(72) Inventors: Manav Bhushan, Noida (IN); Sandeep Sibal, Bangalore (IN)

(73) Assignee: Fourth Frontier Technologies Pvt. Ltd., Bangalore (IN)

( * ) Notice: Subject to any disclaimer, the term of this patent is extended or adjusted under 35 U.S.C. 154(b) by 939 days.

(21) Appl. No.: 15/373,753

(22) Filed: Dec. 9, 2016

(65) Prior Publication Data

US 2017/0347894 A1  Dec. 7, 2017

(30) Foreign Application Priority Data

Jun. 3, 2016 (IN) .............................. 201641019151
Jun. 3, 2016 (IN) .............................. 201641019197

(51) Int. Cl.
*A61B 5/0205* (2006.01)
*A61B 5/0452* (2006.01)
(Continued)

(52) U.S. Cl.
CPC .......... *A61B 5/0205* (2013.01); *A61B 5/0022* (2013.01); *A61B 5/0402* (2013.01);
(Continued)

(58) Field of Classification Search
CPC .......... A61B 2562/0219; A61B 5/0022; A61B 5/0205; A61B 5/021; A61B 5/02416;
(Continued)

(56) References Cited

U.S. PATENT DOCUMENTS 6,654,622 B1 * 11/2003 Eberhard .......... A61B 5/14539
600/322
2009/0149763 A1 * 6/2009 Chen .................. A61B 5/02116
600/494
(Continued)

OTHER PUBLICATIONS

AR Kavsaoglu, K Polat, M Hariharan, "Non-invasive prediction of hemoglobin level using machine learning techniques with the PPG signal's characteristics features", Applied Soft Computing, 37, 983-991 (Year: 2015).*
(Continued)

*Primary Examiner* — Michael W Kahelin
*Assistant Examiner* — Vynn V Huh
(74) *Attorney, Agent, or Firm* — Wiggin and Dana LLP; Gregory S. Rosenblatt; Thomas M. Landman

(57) ABSTRACT

The present invention describes a system and method for continuous monitoring of central (aortic) and peripheral Blood Pressure. The system includes a fully mobile, non-invasive, continuous blood pressure monitoring system that includes one or more Biostrip devices affixed on a user, coupled with an application running on a computing device, which is further connected to a web server in the cloud. The system performs various computations on the Biostrip device, or on the gateway device (Smartphone or Smartwatch), or on the Cloud, and provides the user and authorized third parties with various insights about the blood pressure levels of the user. Further, the system enables the user to receive biofeedback training for controlling hypertension, and schedule online appointments, pay online for such appointments, share data the data securely to obtain insights.

2 Claims, 6 Drawing Sheets

Detailed mechanism for data transfer, storage and processing of the Blood Pressure monitoring system in one particular embodiment.

(51) Int. Cl.
*A61B 5/00* (2006.01)
*A61B 5/0402* (2006.01)
*A61B 5/145* (2006.01)
*A61B 5/11* (2006.01)
*A61B 5/024* (2006.01)
*A61B 5/021* (2006.01)
*G16H 40/67* (2018.01)
*G06F 19/00* (2018.01)

(52) U.S. Cl.
CPC .............. *A61B 5/0452* (2013.01); *A61B 5/11* (2013.01); *A61B 5/14542* (2013.01); *A61B 5/14546* (2013.01); *A61B 5/681* (2013.01); *A61B 5/746* (2013.01); *G06F 19/00* (2013.01); *G16H 40/67* (2018.01); *A61B 5/021* (2013.01); *A61B 5/02416* (2013.01); *A61B 5/6832* (2013.01); *A61B 2562/0219* (2013.01)

(58) Field of Classification Search
CPC ....... A61B 5/0402; A61B 5/0452; A61B 5/11; A61B 5/14542; A61B 5/14546; A61B 5/681; A61B 5/6832; A61B 5/746; G06F 19/00; G16H 40/67
See application file for complete search history.

(56) References Cited

U.S. PATENT DOCUMENTS

| | | | |
|---|---|---|---|
| 2010/0160794 A1* | 6/2010 | Banet | A61B 5/02125 600/485 |
| 2011/0066041 A1* | 3/2011 | Pandia | A61B 5/029 600/484 |
| 2014/0107493 A1* | 4/2014 | Yuen | A61B 5/0205 600/473 |
| 2015/0297134 A1* | 10/2015 | Albert | A61B 5/681 600/384 |
| 2016/0345844 A1* | 12/2016 | McCombie | A61B 5/0024 |
| 2017/0011210 A1* | 1/2017 | Cheong | A61B 5/0022 |
| 2018/0092533 A1* | 4/2018 | Yee | A61B 5/1107 |

OTHER PUBLICATIONS

G Shafiq, S Tatinati, WT Ang, KC Veluvolu, "Automatic Identification of Systolic Time Intervals in Seismocardiogram", Nature Scientific Reports, 6:37524, pp. 1-11 (Year: 2016).*

* cited by examiner

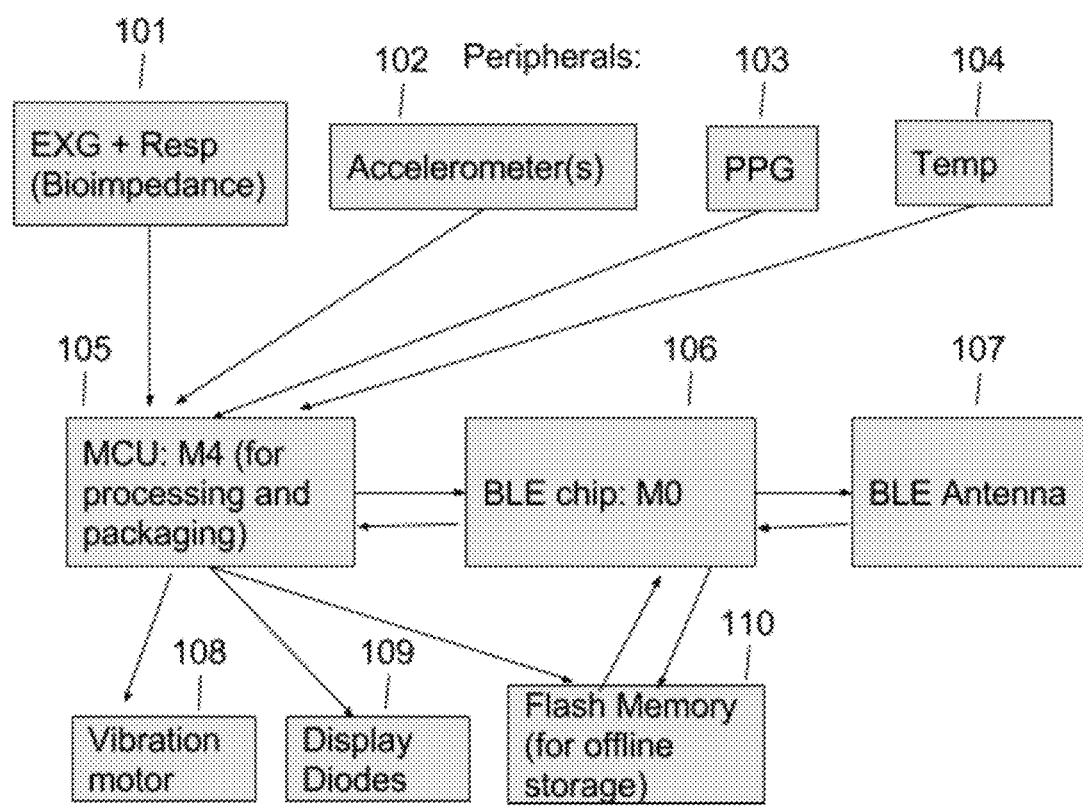
Fig 1: Schematic layout of the device and data transfer protocol in one particular embodiment.

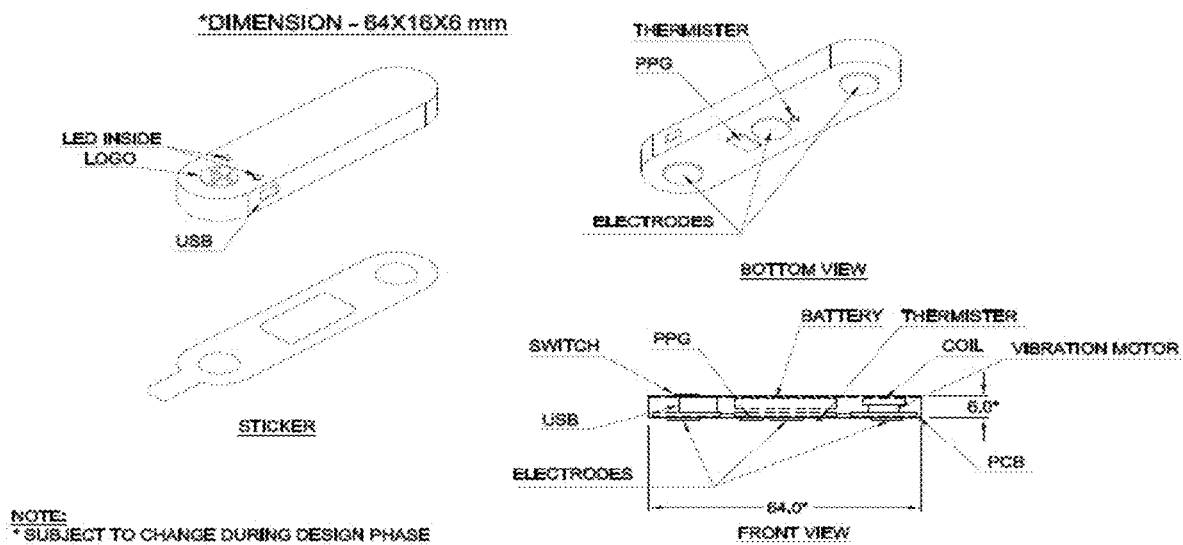
Fig. 2: Biostrip device and sticking mechanism in one embodiment.

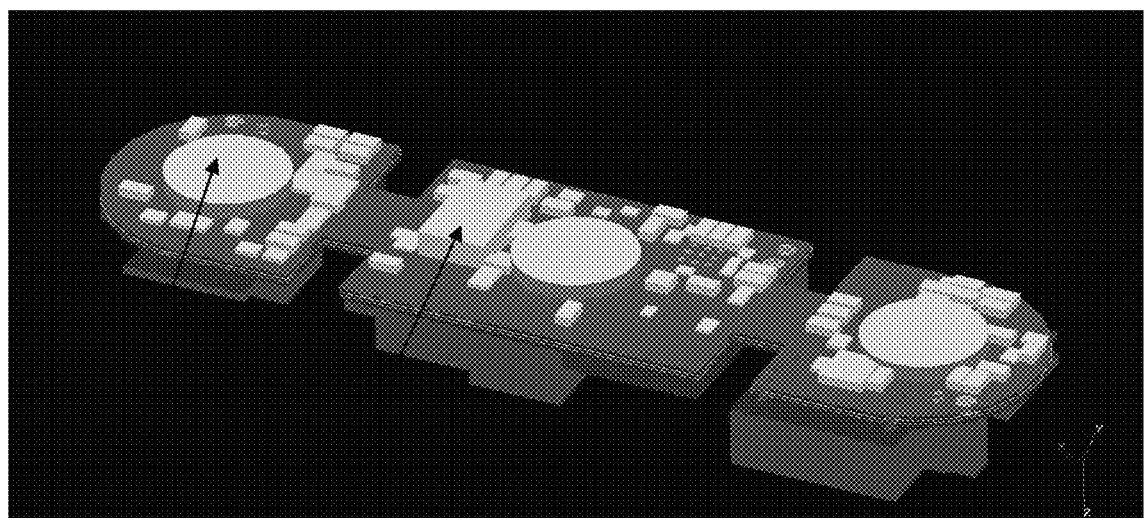
FIG. 3: 3D layout of the device in one embodiment.
111
112

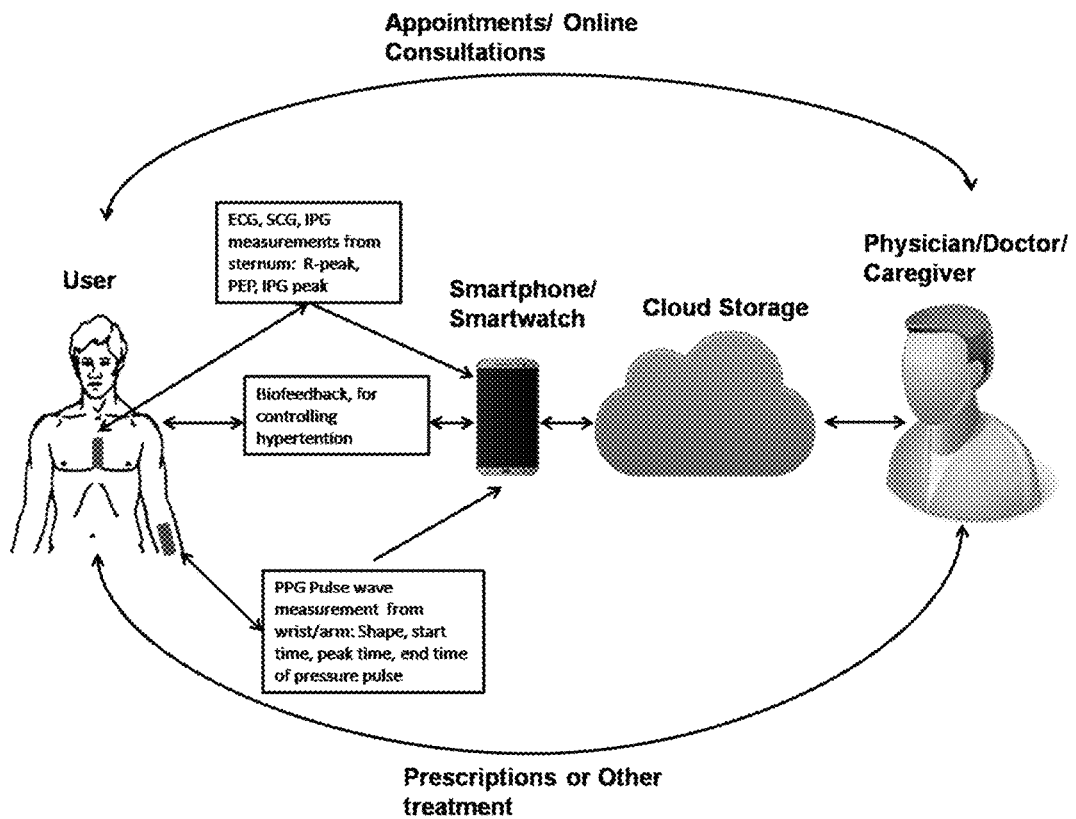
Fig 4: Schematic layout of the complete Blood Pressure monitoring system protocol in one particular embodiment.

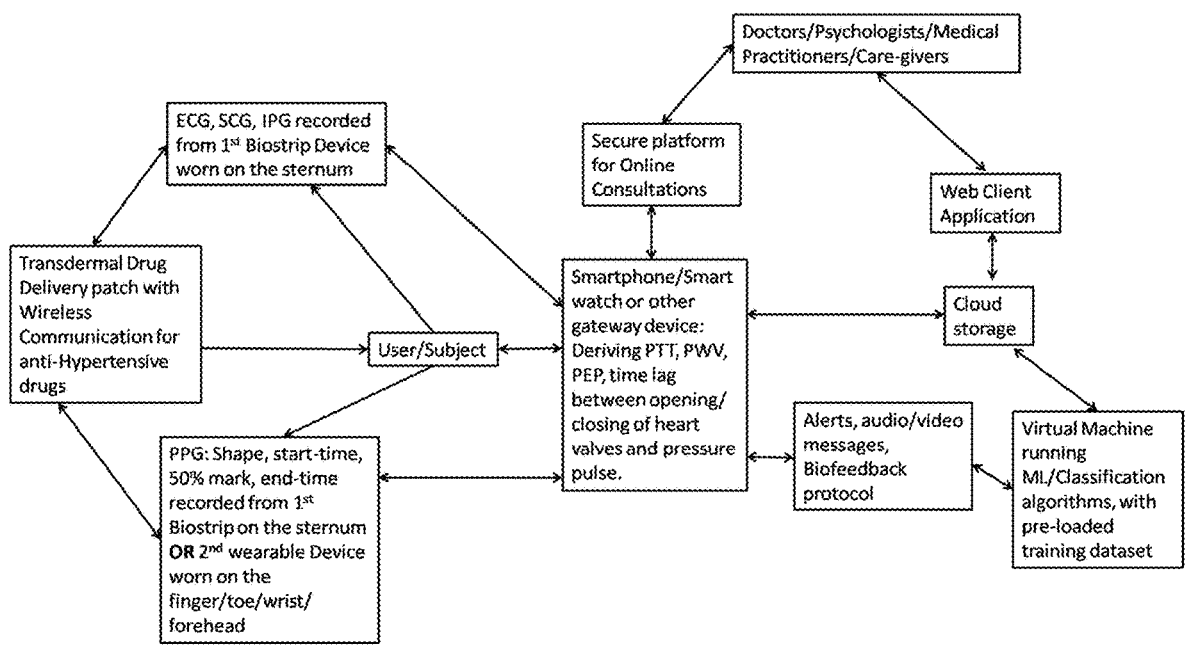
Fig. 5: Detailed mechanism for data transfer, storage and processing of the Blood Pressure monitoring system in one particular embodiment.

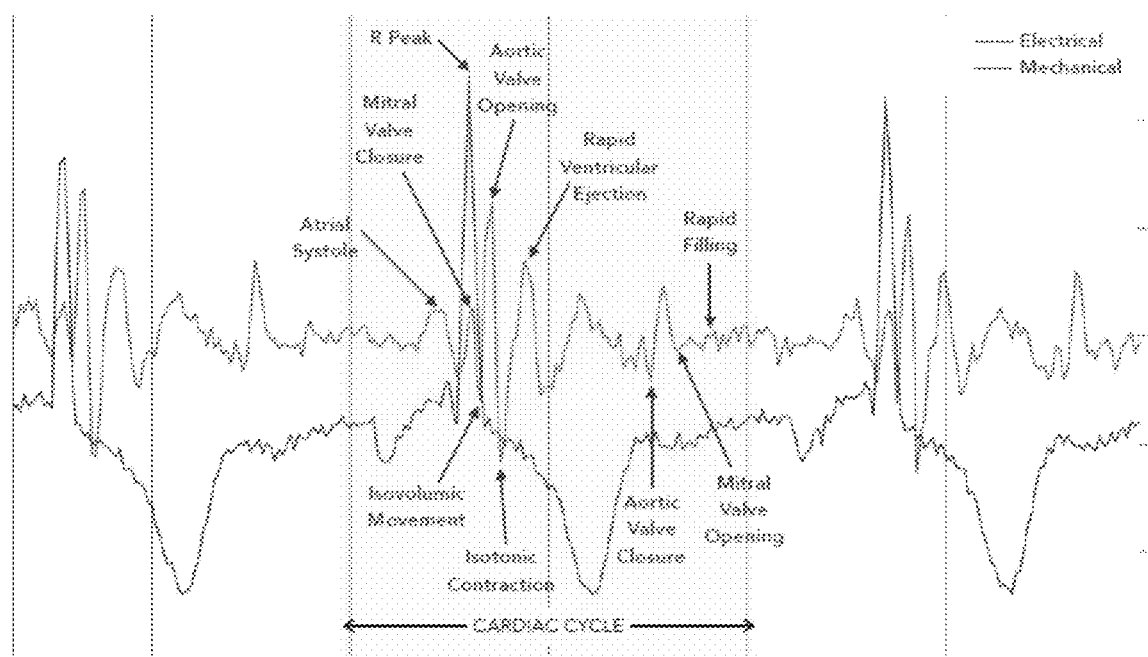
Fig. 6: Detailed cardiac cycle, as observed from the electrical and mechanical sensors present on the Biostrip device placed on the sternum.

SYSTEM AND METHOD FOR CONTINUOUS MONITORING OF BLOOD PRESSURE

TECHNICAL FIELD

The present invention relates generally to medical devices. More particularly, the invention relates to continuous medical monitoring and wearable devices used for monitoring blood pressure.

BACKGROUND OF THE INVENTION

The demand for wearable health monitoring devices and systems is increasing due to rapid development in technology, increasing health costs, aging population, and the like. To address this demand, a variety of prototypes and commercial products have been produced, aimed at providing real-time feedback about the patient's health condition, either to the user himself or to a medical professional, while also being capable of alerting an individual when possible life-threatening health conditions occur.

Conventional wearable systems usually collect medical data from only a single sensor, in periodic increments. Hence, there is a need for a system and method for a wearable device having an efficient and effective monitoring system that collects continuous data. Further, there is a need for a system and method for alerting the patient through a vibration or alerts on a phone or watch.

According to the Health Technology Assessment program, which is part of the NIH, Hypertension is defined as "persistently high blood pressure (BP), with currently accepted thresholds in the UK at 140/90 mmHg. It is one of the most prevalent and powerful risk factors contributing to the development of cardiovascular disease (CVD), and one of the most important preventable causes of premature morbidity and mortality in developed and developing countries. The estimated lifetime risk of middle-aged men and women developing hypertension is 80-90%. The most common type of hypertension is essential hypertension, which has no known cause, and has an estimated prevalence of 30.6%. Currently available treatment options typically include lifestyle changes, dietary restrictions and pharmacological agents.

The predominant measurement technique for measuring BP is through a cuff-based device placed on the upper arm, which occludes the blood flow to measure systolic BP, and then slowly deflates, either mechanically or manually, to measure diastolic BP. However, such a cuff-based device is quite cumbersome, and not conducive for continuous, 24/7 monitoring. Further, the cuff-based monitors measure only peripheral (not central) BP, when it is known that central (aortic) BP is a much better correlate of cardio-vascular disease and other abnormalities. Further, without continuous monitoring of BP, it is impossible to track the effect of different kinds of environmental factors, and therapeutic intervention upon the BP levels.

In order to overcome the challenge of continuous, non-invasive blood pressure measurement, a small self-contained, cuff-less device capable of monitoring central (aortic) and peripheral blood pressure is required.

The above-mentioned shortcomings, disadvantages and problems are addressed herein.

OBJECTS OF THE INVENTION

The various embodiments of the present invention provide a system and method for a continuous health monitoring of a user using a wearable device. An object of the present invention is to provide, and is also one or more of, a wireless, reusable, rechargeable, flexible, light-weight wearable device that monitors various physiological parameters (in particular, Blood Pressure) of the user continuously.

Another object of the present invention is to transmit the monitored data to a computing device such as a smartphone or a smartwatch or other gateway device through wireless communication such as Bluetooth (a trademark of Bluetooth SIG, Inc.), ZigBee (a trademark of the Zigbee Alliance) or other Near-Field Communication ("NFC") protocol.

Yet another object of the present invention is to collect medical quality data from a plurality of sensors including, but not limited to Electromyography ("EMG"), Electrocardiography ("ECG" or "EKG"), Electroencephalography ("EEG"), EXG, respiration, Photoplethysmograph ("PPG") temperature sensors, accelerometers and the like, and transmit the data to the required computing device after initial processing.

Various embodiments of the present invention provide a system and method for a continuous central (aortic) and peripheral blood pressure monitoring system using one or more wearable devices. The system includes one or more wearable devices (referred to herein alternatively as the "Biostrip" device), coupled with an application running on a computing device such as a smartphone, smartwatch, and the like, which is connected to a web server in the cloud, and performs various computations on the wearable device, or the computing device, or a cloud computing device where the data is stored, and more computationally intensive processes are performed.

Another object of the present invention is to combine information obtained by the sensors of the wearable device for analyzing and monitoring blood pressure. This includes processing and cleaning the signal, and quantifying the quality of each individual signal, in a manner described herein.

Yet another object of the present invention is to transmit alerts to the user and to one or more authorized contacts when there is a variation of the blood pressure beyond a pre-determined threshold.

Yet another object of the present invention is to automatically trigger a biofeedback protocol through a mobile application in an audio or a video format, to control the blood pressure of the user.

Yet another object of the present invention is to facilitate automatic storage of the blood pressure data in a secure location on the cloud and allow concerned personnel to view the data easily through a web client.

Yet another object of the present invention is to allow the users to schedule appointments online and pay consultation fees through a payment gateway.

The various embodiments of the present invention provide a system and method for continuous blood pressure monitoring using one or more wearable devices. The present system provides a complete blood pressure monitoring system that has the ability to perform non-invasive, fully mobile, and continuous (as opposed to episodic), cuff-less monitoring of central (aortic) and peripheral blood pressure levels.

The present invention provides a blood pressure monitoring system has the ability to combine information from multiple sensors—ECG, Respiration (from skin impedance), Implantable Pulse Generator ("IPG"), PPG, Galvanic Skin Response device ("GSR"), Electrodermal activity ("EDA"), movement (from accelerometers), seismocardiography ("SCG"), skin temperature, blood glucose, levels of oxygen and haemoglobin in the blood, and hence calculate a very accurate value of blood pressure for each user, and also show correlations with other parameters.

The present invention provides the blood pressure monitoring system described herein allowing the wearable device (biostrip) to send automatic alerts to user, and authorized third party contacts, when abnormal blood pressure levels are detected. Such alerts are delivered by way of messages on the smartphone/smartwatch, or using a display or vibration motor on the device itself.

The present invention includes the ability to automatically trigger a biofeedback protocol through the mobile application in audio/video format, to reduce the blood pressure levels of the user, and control situations of hypertension.

The present invention facilitates automatic storage of all the blood pressure data in a secure location on the cloud, and allows doctors and care-givers to view this data easily through a web client, at their own convenience.

Further, the system allows the user to consult doctors/psychologists or care-givers online, or book appointments with doctors through online, and pay consultation fee through payment gateway, thus completing the loop between diagnosis and treatment.

In one embodiment, the blood pressure monitoring system also couples with a transdermal drug delivery mechanism, and is used to automatically control the dosage of the drug being delivered to treat the user for hypertension or hypotension.

These and other objects and advantages of the present invention will become readily apparent from the following detailed description taken in conjunction with the accompanying drawings.

SUMMARY OF THE INVENTION

The various embodiments of the present invention provide a system and method for continuous health monitoring of the user. The system includes a wearable device that is reusable, rechargeable and coupled with a disposable two-sided sticker, which together form a patch called a 'Biostrip device'. The wearable device includes a plurality of electrodes, an electronic circuitry to measure electric potentials for one or more channels, a circuitry for measuring electric impedance on the skin using electrodes, and one or more accelerometers along with a reflectance-based PPG module. The wearable device is designed to measure the EXG (which refers to a combination of ECG, EEG, and EMG), heart rate, respiration cycles, blood oxygenation, seismocardiography (SCG), subject movements, blood pressure, blood glucose and levels of Haemoglobin (Hb) and other blood gases (such as Carbon Dioxide) of the user.

In particular, the present invention describes a non-invasive, wireless, fully mobile and continuous blood pressure monitoring system that works in conjunction with a plurality of wearable devices, and allows the user to transmit the monitored data securely to a concerned person. The device further allows for scheduling appointments and conducting online consultations with physicians and other medical experts when required. The system monitors health parameters including, but not limited to: ECG, Seismocardiograph (SCG), impedance plethysmography (IPG), electro dermal Activity (EDA), skin temperature, blood oxygenation, and perhaps including: $CO_2$ levels in the blood, haemoglobin levels in the blood and blood glucose levels: to give the user comprehensive information about the blood pressure levels, and variations of the pressure levels in accordance with the other parameters mentioned herein. The system described here has the ability to record medical data from multiple users, and to then use machine learning algorithms to derive insights and provide recommendations for each particular user, and to facilitate online consultations with data sharing.

These and other aspects of the embodiments herein will be better appreciated and understood when considered in conjunction with the following description and the accompanying drawings. It should be understood, however, that the following descriptions, while indicating the preferred embodiments and numerous specific details thereof, are given by way of an illustration and not of a limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIG. 1 is a system diagram illustrating the different component blocks of the Biostrip device, according to one particular embodiment of the present invention.

FIG. 2 illustrates the 3D design, and mechanism for wearing the device, according to one particular embodiment of the present invention. It is to be noted that instead of using a double-sided sticker to affix the device, the device may also be affixed with the help of a strap or other such accompaniment.

FIG. 3 illustrates the 3D layout of the device, according to one particular embodiment of the present invention. The two narrower parts in the middle of the three larger parts indicate the flexible portion of the Biostrip device, which allow it to adhere to irregular surfaces.

FIG. 4 illustrates a system diagram that shows the process of monitoring the blood pressure levels of the user, according to an embodiment of the present invention.

FIG. 5 illustrates a block diagram for the data analysis of the monitored data, according to an embodiment of the present invention.

FIG. 6 shows the ECG signal obtained from the electrical sensors, overlaid with the SCG signal obtained from the mechanical sensors on board the device.

Although the specific features of the present invention are shown in some drawings and not in others. This is done for convenience only as each feature may be combined with any or all of the other features in accordance with the present invention.

DETAILED DESCRIPTION OF THE INVENTION

In the following detailed description, reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments of the present invention provide a system and method for continuous monitoring of a user's health. The system includes a wearable device and corresponding computing device. The wearable device (hereon referred to as the "Biostrip" device) includes an electronic module or a component that is reusable and rechargeable (via micro-USB or wirelessly or both) and is stuck on one side with a two-sided adhesive tape, which is meant for a single use only. For each use, the user peels off one side of the sticker, affixes it to the underside of the device, then peels of the other side, and affixes the wearable device (Biostrip) on himself/herself. The entire wearable device (Biostrip) is thus stuck on the user and is completely wireless and self-contained. Though it is to be noted that in another embodiment, the device may be affixed to different locations on the user's body with the help of flexible straps.

The system includes one or more small wearable, rechargeable Biostrips, along with a gateway device (such as a Smartphone or Smartwatch). One exemplary Biostrip is constructed on three hard printed circuit boards ("PCBs") connected by two flexible connecting PCBs that contain a number of physiological monitors (described below), a processor or microcontroller ("MCU"), a wireless communication hub, a vibration motor, a USB port for charging and data transfer, LEDs, switches, a wireless recharging coil, and several other accompanying components.

The wearable device may include two or more electrodes connected to a single analog front end system, which further transmits the signal to an analog-to-digital converter (ADC) and then on to an MCU, which together measure an electrical signal of the Electro Cardio Gram (ECG) when stuck on the chest, or EEG when stuck on the forehead, or EMG when stuck on a muscle, or a combination of all three. These parameters are collectively referred to herein as EXG.

The Biostrip device includes a reflective Photoplethysmograph ("PPG") module attached to the underside of the device, and in direct visual contact with the skin on the chest/wrist/forehead or other location where the device adheres. The PPG module includes two or more LEDs, and one or more photodiodes, which measure the changes in the intensity of reflected light of different wavelengths. The PPG module is capable of measuring blood oxygenation, as well as levels of Haemoglobin, and other blood gases, such as $CO_2$ and is also capable of measuring heart rate, and other measures derived from changes in blood flow.

The wearable (Biostrip) device includes one or more accelerometers capable of measuring acceleration below a predetermined resolution level. For example, the resolution is set to 0.5 milli-Gs (G-forces, also known as G's, are the units to measure acceleration) or less, and hence capable of measuring steps, breathing, heartbeats, opening and closing of heart valves, and the like, when placed at the sternum. The accelerometer(s) records Seismocardiography (SCG) when affixed to particular parts of the chest. The wearable device (Biostrip) also includes a tap-detection functionality built in, which allow the user to activate different kinds of processes with a single/double tap.

In addition to the above, the Biostrip contains a vibration motor to alert the user under certain predefined circumstances. Alerts are sent when some abnormality is detected from the bio-signals being recorded—either on the device itself in real-time, or on the cloud, or on the findings of a doctor looking at the database on the web client.

The Biostrip contains one or more LEDs, visible through the casing, or placed on top of the casing, which communicates different information about the device status and functionality to the user.

The Biostrip contains a microprocessor or other processor to collect data from the multiple sensors, which implements a series of algorithms on the wearable device itself. The Biostrip also contains an integrated circuit for wireless data communication that enables it to connect and communicate, and send to and receive data from, a smartphone/smartwatch or another gateway device such as a wifi router. The wearable device is charged through a micro-USB connection, or through a wireless charger, and hence can be reused many times. The Biostrip also contains a memory chip that allows it to store data for long periods of time, and then to communicate this saved data to other locations.

The Biostrip device, as part of the Blood Pressure monitoring system, monitors health parameters including, but not limited to: ECG, seismocardiograph (SCG), skin impedance, impedance plethysmography (IPG), pulse plethysmograph (PPG), galvanic skin response (GSR), electro dermal activity (EDA), subject orientation and subject motion, to calculate a value of blood pressure.

In addition to the above, the system records skin temperature, blood oxygenation, $CO_2$ levels in the blood, haemoglobin levels in the blood, blood glucose, in order to provide the user with more detailed information on the blood pressure levels are varying with detailed inputs on how the BP levels are varying with respect to the other physiological parameters mentioned above.

In one embodiment, the blood pressure is calculated from a combination of: (a) the pulse transit time (PTT), calculated as the delay between the R-peak of the ECG, and the beginning, or the half-way point, or the peak of the PPG pulse; (b) pulse wave velocity, calculated as the estimated distance travelled by the blood between the heart and the sternum, divided by the PTT calculated as stated above; (c) the Pre Ejection Period (PEP), measured from the difference between the R-peak measured from the ECG, and the mechanical heart beat measured from the accelerometer in the SCG; (d) the time delay between the R-peak as measured from the ECG, and the peak measured from the IPG; (e) time delays between the opening and closing of the valves, as measured from the SCG, and time-lag between the valve opening and the R-peak as measured from the ECG, and the peak of the Pulse wave, as measured from the PPG; all measured on a single device affixed on the sternum of the subject, and combined with individual factors such as age, sex, height, weight and medical conditions of the user.

In another embodiment, the blood pressure is calculated from a combination of measurements from two wearable (bio-strip) devices: one affixed on the sternum, and measuring ECG, SCG, IPG, and another one affixed on the wrist or forehead or other part of the exposed skin, measuring PPG. According to an embodiment of the present invention, all values measured from the delay between the PPG pulse and the R-peak of the ECG or heartbeat from the SCG or valve openings from the SCG or peak of the IPG are adjusted for the increased distance between the two devices, and individual factors such as age, sex, height, weight and medical conditions of the user.

According to an embodiment of the present invention, the blood pressure is calculated by using a linear or quadratic or logarithmic equation that combines the values of PEP, PWV (or PTT), the heart rate at that instant, respiration rate, shape of the PPG pulse wave, as well as other quantities measured from one or more wearable devices.

In another embodiment, a dataset containing PTT/PWV and PEP values, along with actual systolic and diastolic BP measurements, is used as a training set, and instantaneous measurements of PEP, PWV (or PTT), the heart-rate, respiration rate, shape of the PPG pulse wave, as well as other quantities measured from one or more wearable devices, are combined with individual factors such as age, sex, height, weight, and the like, and then used as inputs for a regression model, to obtain a value for systolic and diastolic BP.

In one instance, where the User is wearing a single Biostrip on the sternum measuring ECG, PPG and SCG, the equation used to derive systolic and diastolic central (aortic) BP are of the form:

$$SBP = x_1 * PWV_{peak} + x_2 * PEP + x_3 * IHR + x_4 * amp(AO) + x_5 * amp(PPG) + x_6 * LVET + x_7 * SCG_{\_XZ} + x_8 * PPG_{foot\text{-}peak} + x_9 * Height + x_{10} * Weight + x_{11} * Age + x_{12} * PPG_{W50} + x_{13} * PPG_{W75} + MC$$

$$DBP = y_1 * PWV_{foot} + y_2 * PEP + y_3 * IHR + y_4 * amp(AO) + y_5 * amp(PPG) + y_6 * LVET + y_7 * SCG_{\_XZ} + y_8 * PPG_{foot\text{-}peak} + y_9 * Height + y_{10} * Weight + y_{11} * Age + y_{12} * PPG_{W50} + y_{13} * PPG_{W75} + MC$$

The equation may adjusted as needed. Here, $PWV_{peak}$ refers to the Pulse Wave Velocity, as measured between the R-peak of the ECG, and the peak of the Pulse Wave in the arterioles at the sternum (near the xiphoid process, or on the manubrium); $PWV_{foot}$ refers to the Pulse Wave Velocity, as measured between the R-peak of the ECG, and the foot (or beginning) of the Pulse Wave in the arterioles at the sternum (near the xiphoid process, or on the manubrium); PEP refers to the Pre-Ejection Period, or the time interval between the R-peak of the ECG and the AO opening peak of the SCG; IHR is the Instantaneous Heart Rate; LVET is the Left Ventricular Ejection Time, measured as the time interval between the Aortic valve opening and closing; $SCG_{\_XZ}$ is the time interval between the beginning of the peak on the X-axis of the SCG, and the mid-point of the Z-axis of the SCG; $PPG_{foot\text{-}peak}$ is the time delay between the foot and peak of the PPG curve; $PPG_{W50}$ is the width of the PPG pulse (as a proportion of one hear-beat cycle) when it is at 50% of the peak value; $PPG_{W75}$ is the width of the PPG pulse (as a proportion of one hear-beat cycle) when it is at 75% of the peak value; and MC is a constant that is dependent on the prior medical conditions of the patient.

The constants $x_i$ and $y_i$ in the above equations are derived from a training set containing data for over 100 patients with data recorded for ECG, PPG, SCG and SBP and DBP, over a 1-4 hour interval, using a Linear Regression Machine Learning algorithm.

In another instance, where the user is wearing a single Biostrip on the sternum measuring ECG, PPG and SCG, the equation used to derive systolic and diastolic central (aortic) BP are of the form:

$$SBP = x_1 * \log_e(a_1(PWV)) + x_2 * PEP + x_3 * IHR + x_4 * amp(AO) + x_5 * amp(PPG) + x_6 * LVET + x_7 * SCG_{\_XZ} + x_8 * Height + x_9 * Weight + x_{10} * Age + MC$$

$$DBP = y_1 * \log_e(a_2(PWV)) + y_2 * PEP + y_3 * IHR + y_4 * amp(AO) + y_5 * amp(PPG) + y_6 * LVET + y_7 * SCG_{\_XZ} + y_8 * Height + y_9 * Weight + y_{10} * Age + MC$$

It should be noted that other forms or variations of the equation are also contemplated by the invention. Here, PWV refers to the Pulse Wave Velocity, as measured between the R-peak of the ECG, and the arrival of the Pulse Wave in the arterioles at the sternum (near the Xiphoid process, or on the manubrium); PEP refers to the Pre-Ejection Period, or the time interval between the R-peak of the ECG and the AO opening peak of the SCG; IHR is the Instantaneous Heart Rate; LVET is the Left Ventricular Ejection Time, measured as the time interval between the Aortic valve opening and closing; $SCG_{\_XZ}$ is the time interval between the beginning of the peak on the X-axis of the SCG, and the mid-point of the Z-axis of the SCG; and MC is a constant that is dependent on the prior medical conditions of the patient.

The constants $x_i$ and $y_i$ in the above equations are derived from a Training set containing data for over 100 patients with data recorded for ECG, PPG, SCG and SBP and DBP, over a 1-4 hour interval, using a Linear Regression Machine Learning algorithm.

In another instance, where the user is wearing a single Biostrip on the sternum measuring ECG, PPG and SCG, the equation used to derive systolic and diastolic central (aortic) BP are Quadratic variations of the equation described above. This equation is of the form:

$$SBP = x_1 * PWV_{peak} + x_2 * PEP + x_3 * IHR + x_4 * amp(AO) + x_5 * amp(PPG) + x_6 * LVET + x_7 * SCG_{\_XZ} + x_8 * Height + x_9 * Weight + x_{10} * Age + x_{11} * (PWV)^2 + x_{12} * (PEP)^2 + x_{13} * (IHR)^2 + x_{14} * (amp(AO))^2 + x_{15} * amp((PPG))^2 + x_{16} * (LVET)^2 + x_{17} * (SCG_{\_XZ})^2 + MC$$

$$DBP = y_1 * PWV_{foot} + y_2 * PEP + y_3 * IHR + y_4 * amp(AO) + y_5 * amp(PPG) + y_6 * LVET + y_7 * SCG_{\_XZ} + y_8 * Height + y_9 * Weight + y_{10} * Age + y_{11} * (PWV)^2 + y_{12} * (PEP)^2 + y_{13} * (IHR)^2 + y_{14} * (amp(AO))^2 + y_{15} * amp((PPG))^2 + y_{16} * (LVET)^2 + y_{17} * (SCG_{\_XZ})^2 + MC$$

Here, PWV refers to the Pulse Wave Velocity, as measured between the R-peak of the ECG, and the arrival of the Pulse Wave in the arterioles at the sternum (near the Xiphoid process, or on the manubrium); PEP refers to the Pre-Ejection Period, or the time interval between the R-peak of the ECG and the AO opening peak of the SCG; IHR is the Instantaneous Heart Rate; LVET is the Left Ventricular Ejection Time, measured as the time interval between the Aortic valve opening and closing; $SCG_{\_XZ}$ is the time interval between the beginning of the peak on the X-axis of the SCG, and the mid-point of the Z-axis of the SCG; and MC is a constant that is dependent on the prior medical conditions of the patient.

The constants $x_i$ and $y_i$ in the above equations are derived from a training set containing data for over 50 patients with data recorded for ECG, PPG, SCG and SBP and DBP, over a 1-4 hour interval, using a Quadratic Regression Machine Learning algorithm.

In another instance, where the user is wearing a single Biostrip on the sternum measuring ECG, PPG and SCG, the equation used to derive systolic and diastolic central (aortic) BP are of the form:

$$SBP = f_1(IHR, PWV_{peak}, PEP, LVET, amp(AO), amp(PPG), SCG_{\_XZ}, Age, Height, Weight)$$

$$DBP = f_2(IHR, PWV_{foot}, PEP, LVET, amp(AO), amp(PPG), SCG_{\_XZ}, Age, Height, Weight)$$

Here $f_1$ and $f_2$ are derived from variants of: a) Support Vector Machine; b) Bayesian Ridge Regression Model; c) K-Nearest-Neighbours Regression Model; d) Random Forest Regression model.

In another instance, where the user is wearing a single Biostrip on the sternum measuring only ECG and SCG, the equation used to derive systolic and diastolic central (aortic) BP are of the form given in [43]-[46] with $x_1$, $x_5$ and $y_1$, $y_5$ are set to 0, or of the form:

$$SBP = f_1(IHR, PEP, LVET, amp(AO), SCG_{\_XZ}, Age, Height, Weight)$$

$$DBP = f_2(IHR, PEP, LVET, amp(AO), SCG_{\_XZ}, Age, Height, Weight)$$

Here $f_1$ and $f_2$ are derived from variants of: a) Support Vector Machine; b) Bayesian Ridge Regression Model; c) K-Nearest-Neighbours Regression Model; d) Random Forest Regression model.

In another instance, where the user is wearing a single Biostrip on the sternum measuring only SCG, the equation used to derive systolic and diastolic central (aortic) BP are of the form given in [43]-[46] with $x_1$, $x_2$, $x_5$ and $y_1$, $y_2$, $y_5$ are set to 0, or of the form:

SBP=$f_1$(IHR,LVET,amp(AO),SCG$_{\_XZ}$,Age,Height, Weight)

DBP=$f_2$(IHR,LVET,amp(AO),SCG$_{\_XZ}$,Age,Height, Weight)

Here $f_1$ and $f_2$ are derived from variants of: a) Support Vector Machine; b) Bayesian Ridge Regression Model; c) K-Nearest-Neighbours Regression Model; d) Random Forest Regression model.

In one particular embodiment, where the user is wearing only one Biostrip on the sternum, measuring only ECG and SCG, the Pulse Transit Time between the opening of the aortic valve, and the time-point at which the pressure pulse hits the aortic arch, is determined by the time-gap between the AO peak on the Z-axis plot of the SCG, and the sharp peak immediately after that, on the Y-axis of the SCG, which denotes the time of arrival of the pressure pulse, at the aortic arch. This interval, denoted by SCG$_{YZ}$, provides the PWV measured in the aorta itself, which can be used with calibration, or with a population-based model, to calculate central (aortic) blood pressure in the following manner:

SBP=$f_1$(IHR,LVET,amp(AO),SCG$_{YZ}$,Age,Height, Weight)DBP=$f_2$(IHR,LVET,amp(AO),SCG$_{YZ}$, Age,Height,Weight)

In another instance, the central (aortic) SBP and DBP values are calculated in exactly the same way described above, except that: (1) PWV is replaced by PWV$_{\_hw}$, which is the value of PWV normalized for Height and Weight; (2) PEP is replaced by PEP$_{\_hw}$, which is the value of PEP normalized for Height and Weight; (3) IHR is replaced by IHR$_{\_age}$, which is the value of IHR normalized for age; and (4) the constants $x_8$, $x_9$, $x_{10}$ and $y_8$, $y_9$, $y_{10}$ are set to 0.

In another embodiment, SBP and DBP are calculated in the manner described above, except with the difference that the constants $x_i$ and $y_i$ from the above equations are determined by calibrating the system against a regular cuff-based BP monitor, or an invasive arterial BP monitor for each individual, instead of determining the values from a population-based regression model.

In the calibration based approach, values for the constants $x_i$ and $y_i$ from above may be determined by asking the User to measure their BP using a standard device (such as the Omron BP monitor), while wearing the Biostrip, in different orientations. For example, User may be asked to measure systolic and diastolic BP three times each while standing, sitting and lying down. Each calibration method will result in one individual regression model, with its own set of constants $\{x_i\}$ and $\{y_i\}$.

In another instance, where the user is wearing two Biostrips, one on the sternum, measuring ECG and SCG, and one on the wrist measuring PPG, the peripheral SBP and DBP values are calculated using the same mathematical models described above, but where PWV is measured between the R-peak of the ECG (measured anywhere on the chest) or the AO peak measured from the SCG on the sternum, and arrival of the Pulse Wave on the wrist.

In another instance, where the user is wearing two Biostrips, one on the sternum, measuring ECG and SCG, and one on the forehead measuring PPG, the peripheral SBP and DBP values are calculated using the same mathematical models described above, but where PWV is measured between the R-peak of the ECG (measured anywhere on the chest) or the AO peak measured from the SCG on the sternum, and the arrival of the pulse wave on the forehead.

In one particular embodiment, where the user is wearing two Biostrips or other wearable devices containing only an accelerometer and a wireless communication module, one on the sternum, measuring SCG, and one on the wrist measuring mechanical movements of the pulse, the peripheral (not central) SBP and DBP values are calculated using the same mathematical models described above, but where PWV is measured between the AO peak measured from the SCG on the sternum, and the mechanical pulse wave measured on the wrist with the accelerometer. In this case, the constants $x_2$, $x_5$ and $y_2$, $y_5$ are set to 0.

In one particular embodiment, the user is wearing two Biostrips, or other wearable devices containing only an accelerometer and a wireless communication module, one on either wrist, measuring mechanical movements of the pulse. In this case, the time delay between the arrival of the pulse wave on one wrist, in comparison with the other wrist, is used in place of PTT in the models described. In this case, the SBP and DBP values are calculated using the values of PTT$_{foot\text{-}foot}$, PTT$_{peak\text{-}foot}$, PTT$_{foot\text{-}peak}$, and PTT$_{peak\text{-}peak}$, and the difference between the them, where the foot and peak are always of different wrists. Abnormal values of the above mentioned factors may also be used to trigger an alert for the User, to indicate possible Ischemia or other cardio-vascular disease in one branch of blood vessels.

In one particular embodiment, the Blood Pressure is estimated while the User holds the Biostrip in his hands, with the left index finger covering one electrode on the left, and the right index finger covering the right-most electrode and the central electrode and the PPG sensor (which falls between the right-most electrode and the central electrode) at the same time. This is an episodic measurement of Blood Pressure, where the user holds the device in this manner for at least 30 seconds, and PTT is calculated by the delay between the R-peak on the ECG, and the foot/peak/50% mark of the PPG curve measured on the index finger. This is converted into PWV by dividing by the distance between the heart and the finger (which is estimated from the subject's height and weight). The PWV$_{foot}$ and PWV$_{peak}$ is then used to estimate systolic and diastolic BP based on: (a) calibration based method for each individual; (b) population-based regression model using factors such as height, weight, age, gender and prior medical history.

In one particular embodiment, the Biostrip attached to the sternum is used to measure ECG and SCG, to determine the values of PEP, LVET, Amp(AO), systolic time, diastolic time, etc, and the User puts his finger on the LED on a smartphone to measure PPG, and the 4F application running on the phone estimates the PTT from the R-peak and Aortic Valve opening measured on the Biostrip, and the foot and peak of the PPG curve as measured on the smartphone. The equation used to determine SBP and DBP are of the form described above, but the constants determined take into account the larger distance between the Heart and the wrist, and the measurement obtained is for peripheral blood pressure, as opposed to central (aortic) blood pressure.

In another embodiment, the blood pressure is calculated from a combination of measurements of the Biostrip device affixed on the sternum, and measuring ECG, SCG, IPG; and another ring-shaped device worn on one of the fingers or toes of the user, measuring PPG on the finger/toe. According to an embodiment of the present invention, the values measured from the delay between the PPG pulse and the R-peak of the ECG or heartbeat from the SCG or valve openings from the SCG or peak of the IPG are adjusted for the increased distance between the heart and the finger/toe of the user, and individual factors such as age, sex, height, weight and medical conditions of the user.

The ring-shaped device mentioned in the above embodiment contains at least two LEDs emitting light at different wavelengths, one photodiode making measurements at regular intervals, a Bluetooth or other NFC module communicating data to the computing device in a wireless manner, and a battery to run all of the above. This device includes a plurality of other sensors, and the operation is synchronised with the operation of the wearable (bio-strip) device affixed on the sternum.

In one embodiment of the system, the processor running on the device first collects data from all the sensors, and also performs signal processing and cleaning, using one of the following protocols:

a) Calculate the SSD (sum of squared differences) value of the Histogram of the measured signal and Histogram of the ideal ECG signal ($ECG_i$, after applying a Bandpass filter with a low cut-off of 2 Hz, and a high cut-off of 30 Hz, using 20 bins, two times the sampling frequency ("2×fs") samples for the Histogram, and 8×fs or 4×fs number of samples in each window for the Bandpass filter (e.g. 1000 or 500 sample window for a sampling rate of 125 Hz). The Histogram of the ideal ECG signal is stored in the CPU memory before-hand, to perform this estimation. Signal quality of a 2×fs sample window is now calculated to be:

Signal_Quality($X$)=max{0,[(20−SSD($X$,$ECG_i$)/$X$)/20× 100]}

This assumes an threshold of 20, or in other words assumes that a Chi-squared value of more than 20 means that the signal is pure noise. However, this threshold may be automatically adjusted based on other measurements.

b) Calculate the FFT of the measured signal X, after applying a Bandpass filter of 2 to 30 Hz, and calculate the SSD value of the FFT of the measured signal, and FFT of the ideal signal ($ECG_i$). This values: SSD(FFT (X), FFT($ECG_i$))/FFT(X), can be used to quantify signal quality in a manner similar to (a) above.

c) In the third method, R-peaks are detected by applying a median filter with window size 2×fs, and then another median filter with window size 7, then subtract it from the original signal.

In one particular embodiment of the invention, the Biostrip device also contains a photoelectric and/or thermoelectric module for harvesting energy from the light or heat in the environment, or the heat emanating from the body, or energy generated from motion. This energy is used to charge the battery, or to run the components of the device itself.

In another embodiment, the device also contains an electronic display, which allows the User to observe different parameters in the device itself. The display may further have the capability to detect the touch of the User, and accept commands using a touchscreen.

In another embodiment, the device contains an acoustic sensor, which allows it to record and process sounds and also perform basic processing on it. This acoustic sensor may be used to record ambient sounds, as well as breathing/wheezing sounds when the device is placed on the chest.

In another embodiment, the device contains a microfluidic sensor that can detect the quantity of different chemicals in sweat, and correlate them with varying values of Blood Pressure to provide more detailed insights to the User. In this embodiment, the microfluidic sensor may detect parameters including, but not limited to: pH levels, chloride levels, lactate levels and glucose levels in the sweat.

In another particular embodiment, the device contains a particulate matter sensor, that can detect and measure the amount of PM2.5 and PM10 particles in the immediate environment of the device, including a specific detection of cigarette smoke in the environment.

According to an embodiment of the present invention, the blood pressure calculated as stated above may be combined with other parameters measured from the device or smartphone or both, and used to diagnose and inform the user if he is in a state of hypertension, and also describe the probable cause of the hypertension. This diagnosis may use a training and classification protocol where the training set is pre-loaded on the web server, and is used to classify the recording from the wearable (Biostrip) devices(s) in real-time, either on the device itself, or on the computing device operated by the user. The training and classification protocol uses algorithms such as Artificial Neural Networks algorithm, Support Vector Machine and a Naive Bayes Classifier.

The blood pressure monitoring system has the ability to combine all the parameters mentioned above, from multiple locations on the body, with each user wearing one or more wearable devices (bio-strip), and thus obtaining derived parameters that combine information from various locations.

The system further includes a system to automatically alert the user, or any authorised third party (friend, family, doctor or other care-giver) when the computed blood pressure levels cross a certain predefined or adaptive threshold, and further trigger a biofeedback protocol shown in the form of an application on the phone or other device to enable the user to regain a low level of blood pressure.

The biofeedback protocol referred to above uses audio or video inputs to the user, delivered through an application running on the computing device of the user, which synchronize with the device affixed on the user via wireless communication protocol.

According to an embodiment of the present invention, the application running on the computing device also trigger other kinds of responses/alerts for the user, upon detecting different levels of blood pressure that are indicative of hypertension, including but not limited to: (a) YouTube videos or other videos stored on the external SD card, or podcasts being played on a theme that is pre-selected by the user, or automatically estimated from the behaviour pattern of the User; (b) songs or other audio tracks played through the smartphone or other multimedia device; (c) jokes displayed on the smartphone.

The system also allows the user, or the caregiver to instantly transfer the stored medical data related to blood pressure, to a concerned physician or caregiver through the application running on the smartphone securely, so that the third party has an option to view the user data on the computing device.

In addition, the system allows the user or the caregiver to instantly book appointments with a concerned doctor at a given hospital or clinic, and also to conduct an 'Online Consultation', by way of an audio/video VOIP call, or a regular phone call, or some other kind of communication protocol over the web.

The blood pressure monitoring system includes the capability of initiating an appointment or online consultation as mentioned above, and also for facilitating the payment for such a service by way of an online payment gateway in a secure manner.

During an online consultation, the system also allows the concerned personnel to view certain parts of the user's data, and to make episodic measurements from the Biostrip device, through instructions delivered to the patient, and thereafter to view the data in real-time through a web application. In this manner, the system facilitates a "Virtual Examination."

The system used information collected from other sensors on the smartphone or tablet or other device, about the user's environment, in order to present the parent or care-giver with a periodic report of the blood pressure levels recorded during different activities, at different times of the day. The application on the phone further gives recommendations to the parent or care-giver for different ways of reducing pain levels at different times of the day.

Additionally, the application running on the phone may also have a mechanism for collecting data from any of the other sensors or applications running on the smartphone, as well as subjective, user-inputted data from the care-giver, as and when the user undergoes different activities, and reaches different blood pressure levels, and other mental/physical states. This data can subsequently be used to improve the recommendations and tips/messages for the same user, as well as other users, while maintaining privacy of data for each user.

The system further uses the information collected from other sensors on computing device, about the environment of the user, in order to present the user and the authorized third-party with periodic report of the user blood pressure levels of the user recorded during different activities, at different times of the day. The application on the phone further gives recommendations to the user or care-giver or the concerned doctor for different ways of controlling blood pressure levels more effectively at different times of the day.

The system stores the individual parameters, such as age, sex, medical history for each user, and combines anonymised information of multiple users from different locations on the cloud, in order to present each individual user with data about the user's blood pressure levels and activities in comparison with a similar population, and in order to give the user information about where they stand with respect to other users, in terms of percentiles and other comparative measures.

The system combines subjective information and information from multiple sensors on multiple users, as described above, to run machine learning algorithms, Bayesian classifiers or other kinds of training and testing protocols, in order to provide alerts that are customized for each individual, based on the normal parameters for users in the same demographic section.

FIG. 1 illustrates a schematic diagram of the invention. A plurality of sensors 101,102,103,104 record data, and transmit the data to a microcontroller 105. The microcontroller may instead be a microprocessor or any other suitable computing device for processing data. The data is processed by the microprocessor 105 and then sent for transmission to the Bluetooth low energy ("BLE")/Wireless transmission module 106. Module 106 communicates the data to a smartphone or another gateway device. In certain embodiments, the microprocessor 105 simply stores the data on the device itself, on a memory chip 110, for transmitting the data at a later time to another device. The wearable (Biostrip) device also contains status diodes 109 which indicate different states of the device, and a vibration motor 108, which can alert the user when configured to do so, either by the MCU or upon receiving an instruction from the smartphone.

FIG. 2 illustrates an exemplary configuration of the device, including the form factor of the device. In one embodiment, the device includes a removable sticker part, which is disposable, and meant to be removed after certain periods of time. According to an embodiment of the present invention, the removable sticker is double sided, and one side affixes to the device, whereas the other side affixed to the skin of the patient.

The wearable device shown in FIG. 2 is flexible, and hence it is able to conform to the shape of the location of the body upon which it is affixed. Further, the sticker shown in FIG. 2 has cut-out holes so that the biomedical sensors affixed on the lower part of the device can be directly in contact with the skin.

FIG. 3 illustrates the 3D layout of the device in one embodiment, including the shape and heights of the different electrical and mechanical components. The lighter top surface denotes the components on the lower side of the device, facing the skin. The three circular objects show the electrodes 111, whereas the light rectangular part shows the optical sensor 112, all of which are directly in contact with the skin when the device is worn.

Further, FIG. 3 shows the electrical components on the upper side of the device, facing away from the subject when worn, on the bottom of the drawing. These components include a microprocessor 105, a Bluetooth module 106, an analog front end for processing the electrical signals, and several other components.

FIG. 4 illustrates one particular embodiment of the device, where the data for ECG, IPG, SCG, respiration, skin temperature and movement is first collected from a wearable device (bio-strip) affixed at the sternum, and data for PPG, hand motion recorded from a second wearable device (bio-strip) affixed on the arm/wrist.

As shown in FIG. 4, data is transferred to the smartphone (or other gateway device), using a wireless communication protocol. According to an embodiment of the present invention, from the computing device such as a smartphone, the data transferred to a secure location on the web (cloud) from where it can be accessed by the authorized third party such as a doctor or a concerned medical professional.

FIG. 4 also illustrates that within the system, the user may directly consult the doctor, or the doctor can send alerts or prescriptions to the user.

As shown in FIG. 5, the monitoring system described in the application combines data from multiple sensors on one or more devices, and transfers it to the smartphone, where values such as PTT, PWV, PEP, and the like are calculated, and subsequently used to calculate the values for systolic and diastolic blood pressure.

FIG. 5 illustrates that this above mentioned data is stored in a centralized, secure database that is HIPAA compliant. This data is then accessed by a virtual machine running various data processing, machine learning and classification algorithms to calculate a more accurate value of Blood Pressure, and also the correlation of Blood Pressure values with other individual or environmental factors.

This virtual machine, shown in FIG. 5, is able to store results in the database, and also send alerts and other messages directly to patients so that they can act appropriately.

As shown in FIG. 5, the virtual machine running classification algorithms triggers a biofeedback protocol, delivered to the patient through the smartphone application, to help in management of stress or chronic pain for the user. The biofeedback protocol mentioned above may also be triggered directly from the smartphone application, without requiring any communication with the cloud.

FIG. 5 also shows that the data used to calculate BP may also be communicated to a Transdermal Drug Delivery system (TDDS), which contains a module for Wireless Communication, so that the dosage of different blood pressure medications being delivered can be regulated automatically by the blood pressure measurements taken through the system.

Further, FIG. 5 shows that the data stored on the cloud database can be accessed by the concerned doctors via a web client application, and the doctors can also send alerts or recommendations directly to the patients.

Additionally, illustrated in FIG. 5 is the concerned doctors and patients can directly interact with each other by way of online consultations or video/audio messages and chats, using a secure channel set up for them to interact and share data with each other.

FIG. 6 shows an example of the electrical and mechanical signals obtained from a functioning Biostrip device placed on the sternum. The red line shows the mechanical signals, which show the opening and closing of the aortic and mitral valves, along with other events from the cardiac cycle. The blue line shows the electrical signals (ECG) obtained on the sternum, which identifies the R-peak, and the PQRS complex. The cardiac time intervals (PEP, LVET, IVRT, IVCT) referred to earlier in the application are calculated as the time difference between these events.

One or more embodiments of the present invention have been described. Nevertheless, it will be understood that various modifications may be made without departing from the spirit and scope of the invention. Accordingly, other embodiments are within the scope of the following claims.

What is claimed is:

1. A wearable device for continuous monitoring of blood pressure, comprising:
    a first component continuously monitoring both electrocardiography (ECG) and seismocardiography (SCG) when affixed to a user's chest;
    a second component continuously monitoring photoplethysmography (PPG) when affixed to a portion of a user's body;
    a processor; and
    an integrated circuit communication hub interconnecting the first component, the second component and the processor to enable a transfer of data;
    the processor synchronizing and combining data from the first component with data from the second component to continuously calculate a blood pressure of the user, wherein the processor calculates systolic central (aortic) blood pressure (SBP) in accordance with:

$$SBP = x_1 * PWV_{peak} + x_2 * PEP + x_3 * IHR + x_4 * amp(AO) + x_5 * amp(PPG) + x_6 * LVET + x_7 * SCG_{-xz} + x_8 * Height + x_9 * Weight + x_{10} * Age + x_{11} * (PWV)^2 + x_{12} * (PEP)^2 + x_{13} * (IHR)^2 + x_{14} * (amp(AO))^2 + x_{15} * amp(PPG))^2 + x_{16} * (LVET)^2 + x_{17} * (SCG_{-xz})^2 + MC$$

where: PWV Pulse Wave Velocity
PEP—Pre-Ejection Period
IHR—Instantaneous Heart Rate
amp(AO)—Amplitude of the Aortic Opening
amp(PPG)—Amplitude of PPG Pulse
LVET—Cardiac Time Interval
SCG—Seismocardiography value
MC—constant dependent on prior medical history of patient
x, y—constants based on training sets of data.

2. The device of claim 1 wherein the processor calculates diastolic central (aortic) blood pressure (DBP) in accordance with:

$$DBP = y_1 * PWV_{foot} + y_2 * PEP + y_3 * IHR + y_4 * amp(AO) + y_5 * amp(PPG) + y_6 * LVET + y_7 * SCG_{-xz} + y_8 * Height + y_9 * Weight + y_{10} * Age + y_{11} * (PWV)^2 + y_{12} * (PEP)^2 + y_{13} * (IHR)^2 + y_{14} * (amp(AO))^2 + y_{15} * amp((PPG))^2 + y_{16} * (LVET)^2 + y_{17} * (SCG_{-xz})^2 + MC.$$

* * * * *